United States Patent
Chappuis et al.

(10) Patent No.: US 10,653,659 B2
(45) Date of Patent: May 19, 2020

(54) COMPOSITIONS COMPRISING A COMPOUND FROM THE FAMILY OF AVERMECTINS AND AN AGONIST COMPOUND FOR AT LEAST ONE OF THE RETINOIC ACID RECEPTORS FOR TREATING ACNE

(71) Applicant: GALDERMA SA, Cham (CH)

(72) Inventors: Jean-Paul Chappuis, Valbonne (FR); Jean Jacovella, Antibes (FR)

(73) Assignee: GALDERMA S.A., Cham (CH)

( * ) Notice: Subject to any disclaimer, the term of this patent is extended or adjusted under 35 U.S.C. 154(b) by 149 days.

(21) Appl. No.: 15/527,873

(22) PCT Filed: Nov. 19, 2015

(86) PCT No.: PCT/EP2015/077157
§ 371 (c)(1),
(2) Date: May 18, 2017

(87) PCT Pub. No.: WO2016/079262
PCT Pub. Date: May 26, 2016

(65) Prior Publication Data
US 2018/0325859 A1    Nov. 15, 2018

(30) Foreign Application Priority Data

Nov. 20, 2014 (FR) ...................... 14 61278
Aug. 6, 2015 (FR) ...................... 15 57587

(51) Int. Cl.
| | | |
|---|---|---|
| *A61K 31/327* | (2006.01) | |
| *A61K 9/00* | (2006.01) | |
| *A61K 31/07* | (2006.01) | |
| *A61K 31/192* | (2006.01) | |
| *A61K 31/203* | (2006.01) | |
| *A61K 31/40* | (2006.01) | |
| *A61K 31/4436* | (2006.01) | |
| *A61K 31/366* | (2006.01) | |
| *A61K 31/232* | (2006.01) | |
| *A61K 31/11* | (2006.01) | |
| *A61P 17/10* | (2006.01) | |
| *A61K 31/7048* | (2006.01) | |

(52) U.S. Cl.
CPC .......... *A61K 31/327* (2013.01); *A61K 9/0014* (2013.01); *A61K 31/07* (2013.01); *A61K 31/11* (2013.01); *A61K 31/192* (2013.01); *A61K 31/203* (2013.01); *A61K 31/232* (2013.01); *A61K 31/366* (2013.01); *A61K 31/40* (2013.01); *A61K 31/4436* (2013.01); *A61K 31/7048* (2013.01); *A61P 17/10* (2018.01)

(58) Field of Classification Search
CPC .......... A61P 17/06; A61P 17/08; A61P 17/10; A61K 31/192; A61K 31/327; A61K 31/40; A61K 31/435; A61K 31/7048
See application file for complete search history.

(56) References Cited

U.S. PATENT DOCUMENTS

| | | | |
|---|---|---|---|
| 6,399,652 B1 * | 6/2002 | Parks ............... | A61K 8/498 514/453 |
| 2002/0061855 A1 | 5/2002 | Parks | |
| 2004/0167084 A1 * | 8/2004 | Parks ............... | A61K 8/498 514/28 |

FOREIGN PATENT DOCUMENTS

| | | |
|---|---|---|
| CN | 102600177 B | 6/2014 |
| EP | 0850909 A1 | 7/1998 |
| FR | 2837101 A1 | 9/2003 |
| FR | 2854074 A1 | 10/2004 |
| WO | 2006/066978 A1 | 6/2006 |

OTHER PUBLICATIONS

International Search Report and Written Opinion of the International Searching Authority dated Apr. 14, 2016 corresponding to International Patent Application No. PCT/EP2015/077157, 17 pages.
Thacher, S.M., et al., "Therapeuic Applications for Ligands of Retinoid Receptors," Current Pharmaceutical Design, vol. 6, No. 1, Jan. 2000, pp. 25-58.
Stein Gold, L., et al., "Efficacy and Safety of Ivermectin 1% Cream in Treatment of Papulopustular Rosacea: Results of Two Randomized, Double-Blind, Vehicle-Controlled Pivotal Studies," Journal of Drugs in Dermatology, vol. 13, No. 3, Mar. 2014, pp. 316-322.
Zhao, Ya-e, et al., "A meta-analysis of association between acne vulgaris and Demodex infestation," Journal of Zhejian University-Science B, vol. 13, No. 3, Mar. 2012, pp. 192-202.

* cited by examiner

*Primary Examiner* — Leigh C Maier
(74) *Attorney, Agent, or Firm* — Sunit Talapatra; Foley & Lardner LLP

(57) ABSTRACT

Compositions including a compound of the family of avermectins, preferably ivermectin, and an agonist compound for at least one of the retinoic acid receptors are described. The compositions are in particular used in the treatment of acne.

6 Claims, 4 Drawing Sheets

COMPOSITIONS COMPRISING A COMPOUND FROM THE FAMILY OF AVERMECTINS AND AN AGONIST COMPOUND FOR AT LEAST ONE OF THE RETINOIC ACID RECEPTORS FOR TREATING ACNE

CROSS-REFERENCE TO PRIOR APPLICATIONS

This application is a National Stage of PCT/EP2015/077157, filed Nov. 19, 2015, and designating the United States (published on May 26, 2016, as WO 2016/079262 A1), which claims priority under 35 U.S.C. § 119 to French Application No. 1461278, filed Nov. 20, 2014, and to French Application No. 1557587, filed Aug. 6, 2015, each hereby expressly incorporated by reference in its entirety and each assigned to the assignee hereof.

The present invention relates to compositions notably used in the treatment of acne.

TECHNOLOGICAL BACKGROUND OF THE INVENTION

Acne is a common multifaceted skin disorder of the hair follicles and sebaceous glands which leads to the formation of comedones. It affects nearly all adolescents and may also persist into adulthood. Adult women may particularly be affected and experience premenstrual outbreaks.

Genetic predisposition, overproduction of sebum (seborrhea), androgens, follicular keratinization disorders (comedogenesis) and bacterial colonization accompanied by inflammatory factors are various factors which play a determining role in the formation of acne.

Several forms of acne exist, the factor common to all of them being the attack of pilosebaceous follicles. For example, mention may be made of acne conglobata, acne keloidalis nuchae, drug-induced acne, recurrent acne miliaris, acne necrotica, acne neonatorum, premenstrual acne, occupational acne, senile acne, solar acne and acne vulgaris.

Acne vulgaris, also known as polymorphous juvenile acne, is the most common and comprises four stages:
  stage 1 corresponds to comedonal acne and is characterized by a large number of microcysts and open and/or closed comedones;
  stage 2, or papulopustular acne, is mildly to moderately serious and is characterized by the presence of microcysts and open and/or closed comedones, but also red papules and pustules. It affects mainly the face and leaves some scars;
  stage 3, or papulocomedonal acne, is more serious and extends to the back, thorax and shoulders. It is accompanied by a large number of scars;
  stage 4, or nodulocystic acne, is accompanied by numerous scars. It exhibits nodules and also large, painful purplish pustules.

These various forms of acne are traditionally treated by using various active agents. For example, mention may be made of anti-seborrheic and anti-infective agents such as benzoyl peroxide marketed by Pierre Fabre under the name Eclaran®. Mention may also be made of retinoids such as tretinoin, marketed by Galderma under the name Retacnyl®, or isotretinoin, marketed by Roche Laboratories under the name Roaccutane®, for their capacity to act on keratinocyte proliferation and differentiation. Naphthoic acid derivatives, such as adapalene, described notably in the application FR 2 837 101, or the derivatives thereof, described in the patent EP 0 850 909, are also recognized as active substances for treating acne.

However, the use of these active agents, notably retinoids, causes numerous side effects in patients. In particular, retinoid-based treatments may cause dry skin, irritation, erythema, desquamation and stinging or burning in treated patients. Thus, the use of such treatments also requires the application of multiple moisturizing, humectant and soothing agents to provide relief to the patient.

Moreover, these various treatments are often combined with a course of antibiotics such as tetracycline, erythromycin, minocycline and doxycycline to treat acneic lesions, but their low lipid solubility requires regular and frequent administration which may generate resistance phenomena and promote the development of these resistant organisms as well as intolerance-related problems in the patient.

Thus, it must be acknowledged that there exists a need to provide acne treatments that are more effective and that do not cause side effects in the patient. In particular, there is to date no treatment that acts on both the factors involved in acne formation and the inflammatory reactions resulting therefrom.

SUMMARY OF THE INVENTION

It is to the credit of the Applicant to have discovered that a combination of a compound from the family of avermectins, in particular ivermectin, with an agonist compound for at least one of the retinoic acid receptors, makes it possible to obtain a more effective acne treatment with fewer side effects.

In particular, such a combination makes it possible to act on both inflammatory and noninflammatory acne lesions with a synergistic effect. Furthermore, the combination of these two active agents makes it possible to obtain a clear advantage in terms of efficacy and of patient tolerance by mitigating notably the irritating effect caused by the use of agonist compounds for at least one of the retinoic acid receptors.

The object of the present invention is thus to propose a composition comprising a compound from the family of avermectins and an agonist compound for at least one of the retinoic acid receptors, for use in the treatment of acne.

In a preferred embodiment, the compound from the family of avermectins is ivermectin.

In a first particular embodiment, the agonist compound for at least one of the retinoic acid receptors has the formula (I):

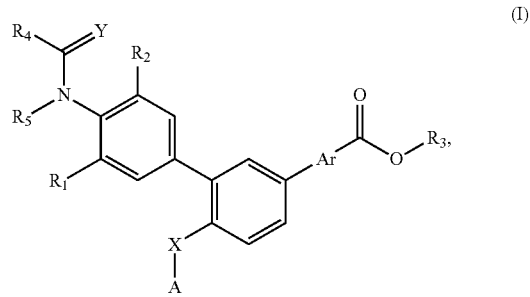

wherein:
  $R_1$ represents a hydrogen atom, an alkyl group having 1 to 4 carbon atoms or a —$CF_3$ group;

$R_2$ represents a hydrogen atom, an alkyl group or alkoxy having 1 to 4 carbon atoms or a chlorine atom;

$R_3$ represents a hydrogen atom, an alkyl or alkoxy group having 1 to 10 carbon atoms and preferably having 1 to 6 carbon atoms, which may be linear or branched, optionally substituted by a methoxy group, or a linear or branched alkyl group having 1 to 10 carbon atoms containing an ether function;

$R_4$ and $R_5$ represent a hydrogen atom or an alkyl group having 1 to 3 carbon atoms, or $R_4$ and $R_5$ may form, together with the bond —N—C(=Y)—, a ring of the pyrrolidine, pyrrolidone, piperidine or piperidone type;

Y represents two hydrogen atoms or a heteroatom, preferably an oxygen or a sulfur;

Ar represents a 1,4-phenyl, 2,5-pyridyl, 5,2-pyridyl or 2,5-thiophenyl ring;

X represents an oxygen atom optionally substituted by an alkyl or alkylamine group having 1 to 4 carbon atoms or a C—C single bond;

A represents a hydrogen atom or the following formula (IA):

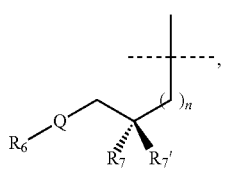

(IA)

wherein:
Q represents an oxygen atom or an —NH— bond;
$R_6$ represents a hydrogen atom, an alkyl group having 1 to 6 carbon atoms, a cycloalkyl group having 3 to 6 carbon atoms or a —C(O)CH$_3$ or —C(O)CH$_2$CH$_3$ group;
$R_7$ and $R_7'$ represent, independently of each other, a hydrogen atom or a hydroxyl group, provided that $R_7$ and $R_7'$ are not simultaneously a hydroxyl group; and n=0, 1, 2, 3, 4 or 5;

and the optical and geometrical isomers of said compound of formula (I) as well as the pharmaceutically acceptable salts thereof.

Preferably, the compound of formula (I) is 3"-tert-butyl-4'-(2-hydroxyethoxy)-4"-pyrrolidin-1-yl-[1,1';3',1"]-terphenyl-4 carboxylic acid.

In a second particular embodiment, the agonist compound for at least one of the retinoic acid receptors has the formula (II):

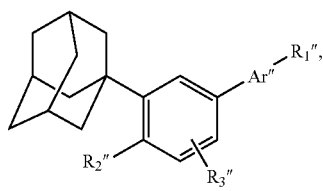

(II)

wherein:
$R_1"$ represents a —CH$_3$ group, a —CH$_2$—O—$R_4"$ group, an —O—$R_4"$ group, a —CO—$R_5"$ group, $R_4"$ and $R_5"$ being as defined below, $Ar"$ represents a group selected from the groups having the following formulae (a) to (f):

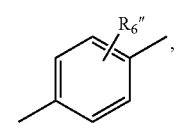

(a)

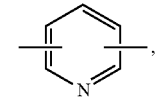

(b)

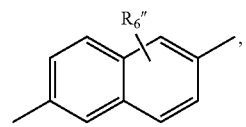

(c)

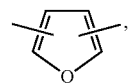

(d)

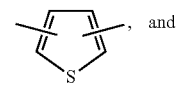

(e) and

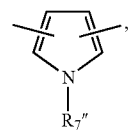

(f)

$R_6"$ and $R_7"$ being as defined below,
$R_2"$ represents the group —OCH$_3$, or —(X)$_m$—(CH$_2$)$_n$—Y—(CH$_2$)$_p$—$R_8"$, the values m, n and p and the groups X, Y and $R_8"$ being as defined below,
$R_3"$ represents a hydrogen atom, a halogen atom, an alkyl group having 1 to 6 carbon atoms or an —O—$R_4"$ group,
$R_4"$ represents a hydrogen atom, an alkyl group having 1 to 6 carbon atoms or a —CO—$R_9"$ group,
$R_5"$ represents a hydrogen atom, an alkyl group having 1 to 6 carbon atoms, an —OR$_{10}"$ group or a

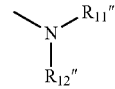

group wherein $R_{11}"$ and $R_{12}"$, which may be the same or different, represent a hydrogen atom, an alkyl group having 1 to 6 carbon atoms, a mono- or polyhydroxyalkyl group, an optionally substituted aryl group, or an amino acid, peptide or sugar residue, or taken together form a heterocycle,
m is an integer equal to 0 or 1,
n is an integer between 1 and 6 inclusive,
p is an integer between 1 and 6 inclusive,
X represents O or S(O)$_q$,
Y represents O, S(O)$_q$ or N—$R_7"$,
q is an integer between 0 and 2 inclusive,
$R_6"$ represents a hydrogen atom, a halogen atom, an alkyl group having 1 to 6 carbon atoms or an —O—$R_4"$ group,
$R_7"$ represents a hydrogen atom, an alkyl group having 1 to 6 carbon atoms or a —CO—$R_9"$ group, $R_8''$ represents a mono- or polyhydroxyalkyl group the hydroxy groups of which are optionally protected in the form of methoxy, ethoxy, acetoxy or acetonide, a —CO—$R_8''$ group, an optionally substituted aryl or aralkyl group, $R_9''$ represents an alkyl group having 1 to 6 carbon atoms, $R_{10}''$ represents a hydrogen atom, an alkyl group, an alkenyl group, a mono- or polyhydroxyalkyl group the hydroxy groups of which are optionally protected in the form of methoxy, ethoxy, acetoxy or acetonide, an optionally substituted aryl or aralkyl group, or a sugar residue, or an amino acid or peptide residue, and the optical and geometrical isomers of said compounds of formula (II) as well as the pharmaceutically acceptable salts thereof.

Preferably, the compound of formula (II) is adapalene.

In a third particular embodiment, the agonist compound for at least one of the retinoic acid receptors has the formula (III):

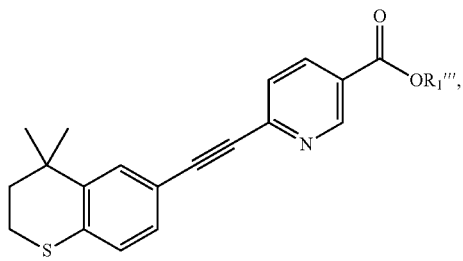

(III)

wherein:

$R_1'''$ represents a hydrogen atom, an alkyl group having 1 to 18 carbon atoms, an alkenyl group having 1 to 18 carbon atoms, an alkynyl group having 1 to 18 carbon atoms, an aryl, heteroaryl, cycloalkyl or heterocycloalkyl group.

Preferably, the compound of formula (III) is tazarotene.

In a fourth particular embodiment, the agonist compound for at least one of the retinoic acid receptors has the formula (IVA) or (IVB):

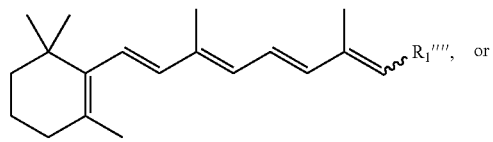

(IVA)

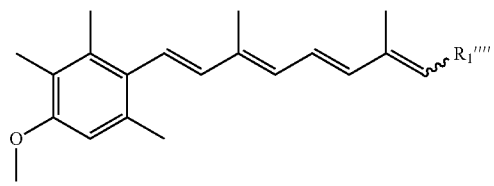

(IVB)

wherein:

$R_1$ represents a —$CH_2OH$ or —CHO group, or a $CO_2R_2$ group wherein $R_2$ represents a hydrogen atom, an alkyl group having 1 to 18 carbon atoms, an alkenyl group having 1 to 18 carbon atoms, an alkynyl group having 1 to 18 carbon atoms, an aryl, heteroaryl, cycloalkyl or heterocycloalkyl group.

Preferably, the compound of formula (IVA) or (IVB) is retinoic acid, retinol, retinal, etretinate or acitretin.

In a fifth particular embodiment, the agonist compound for at least one of the retinoic acid receptors is bexarotene.

In an embodiment, the compound from the family of avermectins present in the compositions of the invention makes up between 0.001 and 10%, preferably between 0.001 and 5%, more preferably between 0.1 and 2%, and still more preferably 1% by weight of the total weight of the composition.

In another embodiment, the agonist compound for at least one of the retinoic acid receptors makes up between 0.001 and 10%, preferably between 0.001 and 5%, more preferably between 0.01 and 1%, and still more preferably 0.1 or 0.3% by weight of the total weight of the composition.

In a preferred embodiment, the compound from the family of avermectins makes up 1% by weight and the agonist compound for at least one of the retinoic acid receptors makes up between 0.1 and 1%, preferably 0.1 or 0.3% by weight of the total weight of the composition.

Particularly, the compositions used in the invention are intended to be administered topically and are preferably in the form of a gel, a lotion or a cream.

Another object of the invention relates to a kit comprising (a) a first composition comprising a compound from the family of avermectins, preferably ivermectin, and (b) a second composition, distinct from the first, comprising an agonist compound for at least one of the retinoic acid receptors, preferably adapalene.

In a preferred embodiment, the kit is used in the treatment of acne.

An additional object of the invention relates to a composition, preferably in topical form, comprising ivermectin and adapalene in a physiologically acceptable medium.

DETAILED DESCRIPTION OF THE INVENTION

Figure 1A:
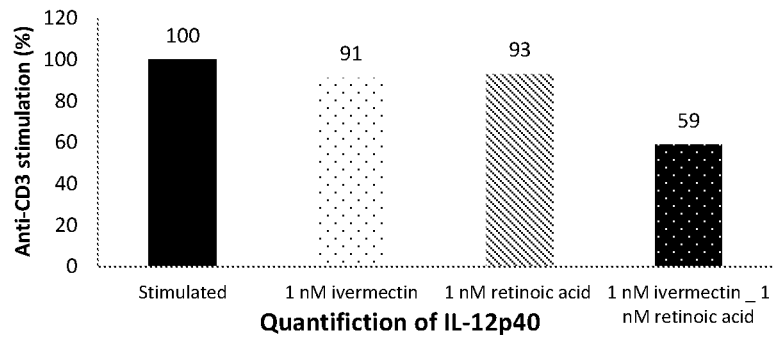
FIGS. 1A to 1C: Quantification of the production of inflammatory cytokines IL12p40 (FIG. 1A), TNFα (FIG. 1B) and IFNγ (FIG. 1C) with ivermectin and retinoic acid alone or in combination.
Figure 1B:
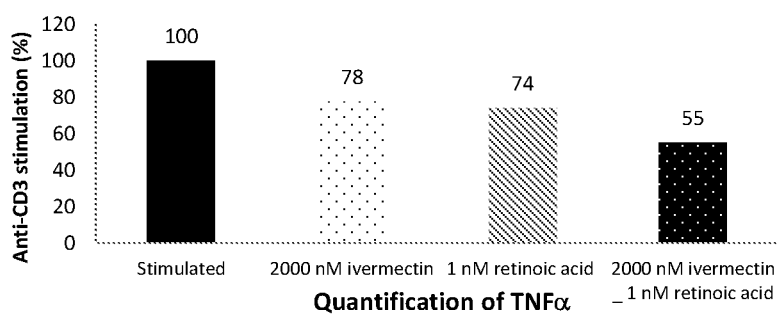
Figure 1C:
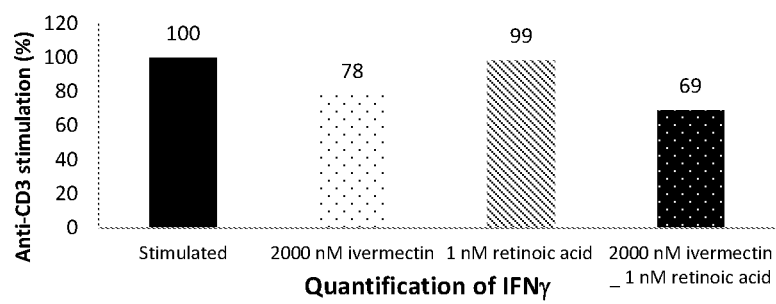
Figure 2A:
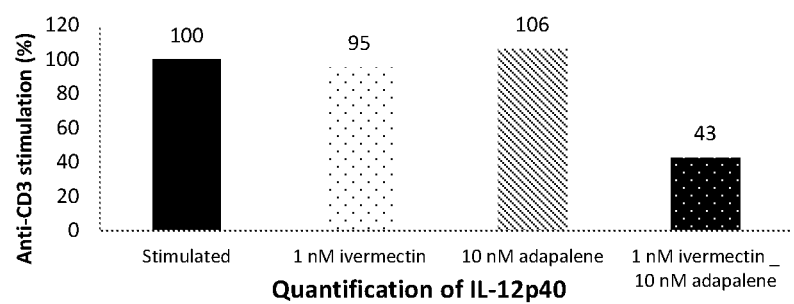
FIGS. 2A and 2B: Quantification of the production of inflammatory cytokines IL12p40 (FIG. 2A) and IFNγ (FIG. 2B) with ivermectin and adapalene alone or in combination.
Figure 2B:
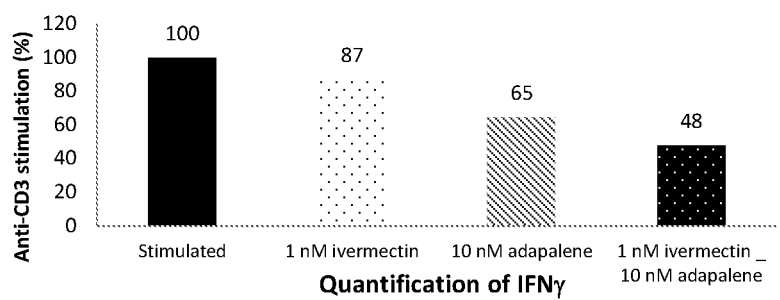
Figure 3A:
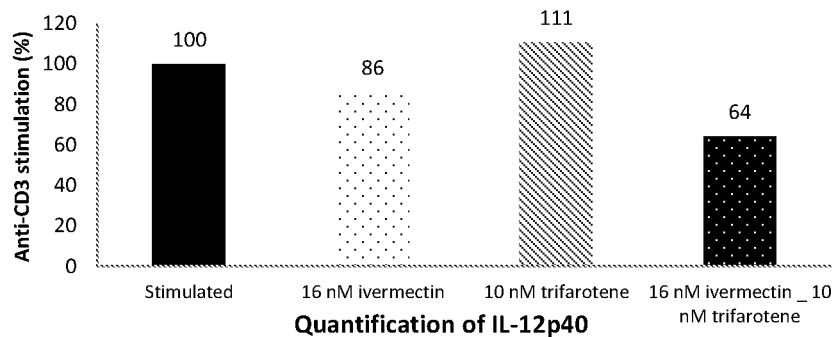
FIGS. 3A-3C: Quantification of the production of inflammatory cytokines IL12p40 (FIG. 3A), TNFα (FIG. 3B) and IFNγ (FIG. 3C) with ivermectin and trifarotene alone or in combination.
Figure 3B:
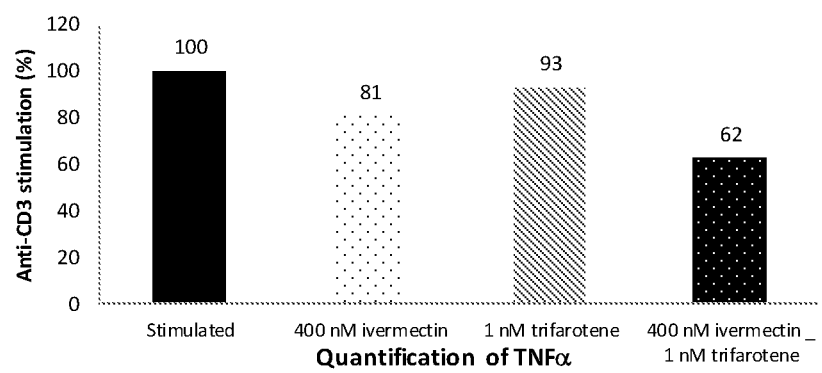
Figure 3C:
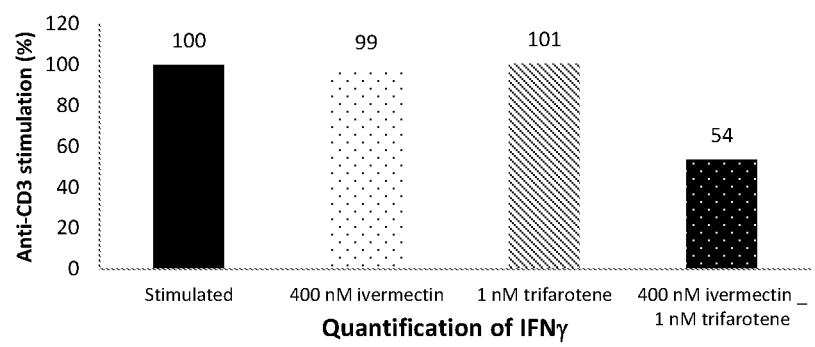
Figure 4A:
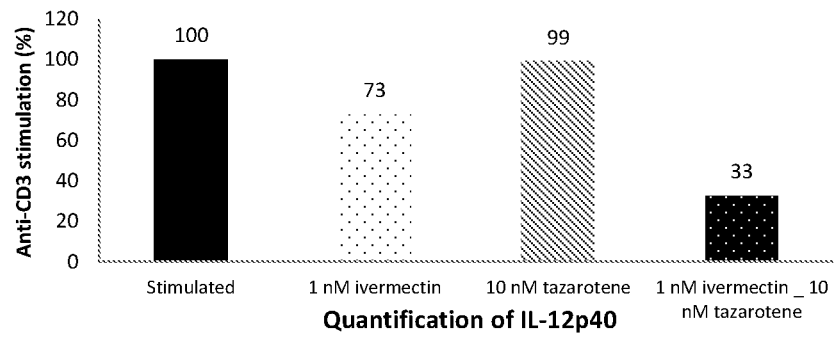
FIGS. 4A-4C: Quantification of the production of inflammatory cytokines IL12p40 (FIG. 4A), TNFα (FIG. 4B) and IFNγ (FIG. 4C) with ivermectin and tazarotene alone or in combination.
Figure 4B:
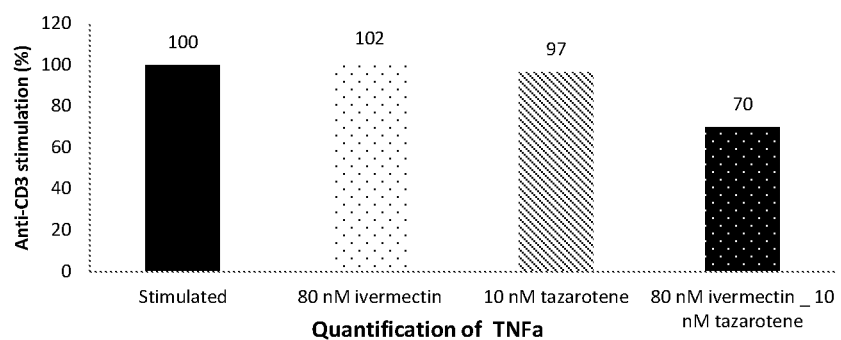
Figure 4C:
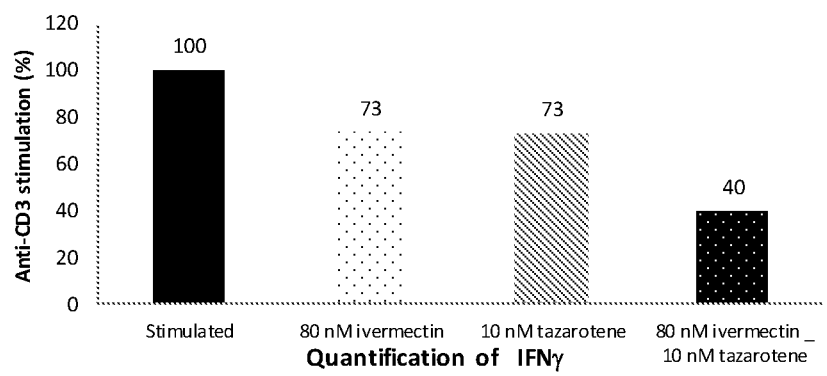

The inventors identified a novel use of a composition in the treatment of acne and surprisingly discovered that the combination of the two active agents, namely a compound from the family of avermectins, in particular ivermectin, and an agonist compound for at least one of the retinoic acid receptors, made it possible to treat acne more effectively. In particular, it was shown that such a combination was effective for treating the various forms of acne, by acting on both inflammatory and noninflammatory lesions, and by improving the treated patient's tolerance, notably by reducing the side effects due to the use of retinoic acid receptor agonists known to be particularly irritating.

The invention thus relates to a composition comprising a compound from the family of avermectins and an agonist compound for at least one of the retinoic acid receptors, for use in the treatment of acne.

The invention also relates to a combination of a compound from the family of avermectins and an agonist compound for at least one of the retinoic acid receptors, for use in the treatment of acne.

The invention also relates to methods or processes implementing a composition comprising a compound from the family of avermectins, preferably ivermectin, and an agonist compound for at least one of the retinoic acid receptors as defined in the present application for administration in a therapeutically effective amount to a patient with acne.

The invention also relates to a method for treating acne comprising administering a therapeutically effective amount of a compound from the family of avermectins, preferably ivermectin, and an agonist compound for at least one of the retinoic acid receptors, to a patient with acne. Preferably, the method comprises administering a composition as defined in the present application comprising the compound from the family of avermectins and the agonist compound for at least one of the retinoic acid receptors in a therapeutically effective amount.

The invention also relates to the use of a composition as defined in the present application comprising a compound from the family of avermectins and an agonist compound for at least one of the retinoic acid receptors for preparing a medicinal product for treating acne.

Retinoic Acid Receptor Agonists

It is well-known that all-trans retinoic acid acts on cell differentiation and proliferation by interacting with nuclear retinoic acid receptors (RARs). RARs activate the transcription of specific genes by binding to elements of the DNA sequence, known as RAR response elements (RAREs), as heterodimers with retinoid X receptors (RXRs). Three subtypes of human RARs have been identified and described: RARα, RARβ and RARγ. Numerous chemical compounds are described in the prior art as being retinoic acid receptor ligands and are used within compositions intended to treat various dermatological disorders.

The dissociation constants are determined by means of traditional tests known to the person skilled in the art. These tests are notably described in the following references: (1) "Selective Synthetic Ligands for Nuclear Retinoic Acid Receptor Subtypes" in Retinoids: Progress in Research and Clinical Applications, Chapter 19 (pp. 261-267), Marcel Dekker Inc., edited by Maria A. Livrea and Lester Packer; (2) "Synthetic Retinoids: Receptor Selectivity and Biological Activity" in Pharmacol Skin, Basel, Karger, 1993, Volume. 5, pp. 117-127; (3) "Selective Synthetic Ligands for Human Nuclear Retinoic Acid Receptors" in Skin Pharmacology, 1992, Vol. 5, pp. 57-65; (4) "Identification of Synthetic Retinoids with Selectivity for Human Nuclear Retinoic Acid Receptors" in Biochemical and Biophysical Research Communications, Vol. 186, No. 2 Jul. 1992, pp. 977-983; and (5) "Selective High Affinity Retinoic Acid Receptor α or β-γ Ligands" in Mol. Pharmacol., Vol. 40, pp. 556-562. The description of these tests is incorporated in the present application for reference.

The test described in the patent FR 2 735 370 makes it possible to identify RXR agonist compounds. The description of this test is incorporated in the present application for reference. This test comprises the following steps:

(i) a sufficient amount of a compound that is an active ligand for at least one receptor of the steroid/thyroid receptor superfamily, other than a specific RXR ligand, and that is able to heterodimerize with RXRs, is applied topically to a portion of the skin of a mammal, notably the ear, (ii) a molecule capable of having RXR agonist activity is administered systemically or topically to this same mammal or this same portion of mammalian skin, before, during or after step (i), and (iii) the response is evaluated on the portion of the mammal's skin thus treated.

Thus, the response to topical application on the ear of a mammal of a compound that is an active ligand for at least one receptor of the steroid/thyroid receptor superfamily, other than a specific RXR ligand, and that is able to heterodimerize with RXRs, which corresponds to an increase in the thickness of said ear, can be inhibited by the systemic or topical administration of an RXR agonist molecule.

In the context of the present invention, by "agonist compound for at least one of the retinoic acid receptors" is meant any compound capable of binding to at least one of the RARs and/or RXRs and whose agonist activity is identified and evaluated in the above-referenced tests and in particular in the patent FR 2 735 370.

In a particular embodiment, the agonist compound for at least one of the retinoic acid receptors has the formula (I):

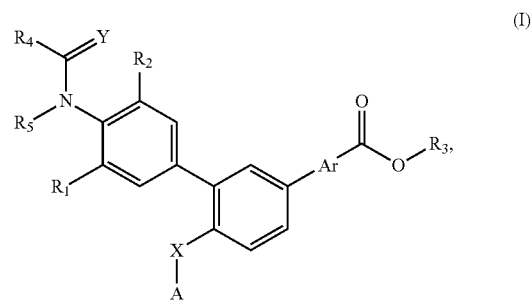

wherein:

$R_1$ represents a hydrogen atom, an alkyl group having 1 to 4 carbon atoms or a —$CF_3$ group;

$R_2$ represents a hydrogen atom, an alkyl or alkoxy group having 1 to 4 carbon atoms or a chlorine atom;

$R_3$ represents a hydrogen atom, an alkyl or alkoxy group having 1 to 10 carbon atoms and preferably having 1 to 6 carbon atoms, which may be linear or branched, optionally substituted by a methoxy group, or a linear or branched alkyl group having 1 to 10 carbon atoms containing an ether function;

$R_4$ and $R_5$ represent a hydrogen atom or an alkyl group having 1 to 3 carbon atoms, or $R_4$ and $R_5$ may form, together with the bond —N—C(=Y)—, a ring of the pyrrolidine, pyrrolidone, piperidine or piperidone type;

Y represents two hydrogen atoms or a heteroatom, preferably an oxygen or a sulfur;

Ar represents a 1,4-phenyl, 2,5-pyridyl, 5,2-pyridyl or 2,5-thiophenyl ring;

X represents an oxygen atom optionally substituted by an alkyl or alkylamine group having 1 to 4 carbon atoms or a C—C single bond;

A represents a hydrogen atom or the following formula (IA):

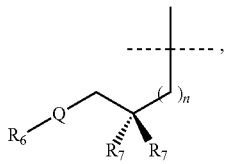
(IA)

wherein:
Q represents an oxygen atom or an —NH— bond;
$R_6$ represents a hydrogen atom, an alkyl group having 1 to 6 carbon atoms, a cycloalkyl group having 3 to 6 carbon atoms or a —C(O)CH$_3$ or —C(O)CH$_2$CH$_3$ group;
$R_7$ and $R_7'$ represent, independently of each other, a hydrogen atom or a hydroxyl group, provided that $R_7$ and $R_7'$ are not simultaneously a hydroxyl group; and
n=0, 1, 2, 3, 4 or 5;
and the optical and geometrical isomers of said compounds of formula (I) as well as the pharmaceutically acceptable salts thereof.

Preferably the agonist compound for at least one of the retinoic acid receptors of formula (I) is a compound described in the patent EP 1 831 149, the description of the compounds being incorporated herein for reference. Still more preferably, the agonist compound for at least one of the retinoic acid receptors of formula (I) is 3"-tert-butyl-4'-(2-hydroxyethoxy)-4"-pyrrolidin-1-yl-[1,1';3',1"]-terphenyl-4-carboxylic acid.

In another particular embodiment, the agonist compound for at least one of the retinoic acid receptors has the formula (II):

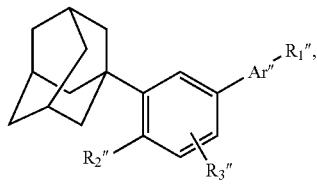
(II)

wherein:
$R_1''$ represents a —CH$_3$ group, a —CH$_2$—O—$R_4''$ group, an —O—$R_4''$ group, a —CO—$R_5''$ group, $R_4''$ and $R_5''$ being as defined below,
Ar" represents a group selected from the groups having the following formulae (a) to (f):

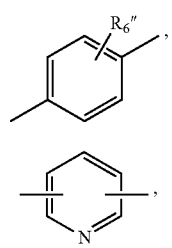
(a)

(b)

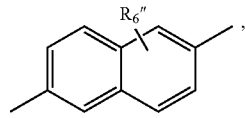
(c)

(d)

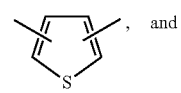
, and
(e)

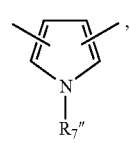
(f)

$R_6''$ and $R_7''$ being as defined below,
$R_2''$ represents the group —OCH$_3$, or —(X)$_m$—(CH$_2$)$_n$—Y—(CH$_2$)$_p$—$R_8''$, the values m, n and p and the groups X, Y and $R_8''$ being as defined below,
$R_3''$ represents a hydrogen atom, a halogen atom, an alkyl group having 1 to 6 carbon atoms or an —O—$R_4''$ group,
$R_4''$ represents a hydrogen atom, an alkyl group having 1 to 6 carbon atoms or a —CO—$R_9''$ group,
$R_5''$ represents a hydrogen atom, an alkyl group having 1 to 6 carbon atoms, an —O$R_{10}''$ group or a

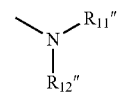

group wherein $R_{11}''$ and $R_{12}''$, which may be identical or different, represent a hydrogen atom, an alkyl group having 1 to 6 carbon atoms, a mono- or polyhydroxyalkyl group, an optionally substituted aryl group, or an amino acid, peptide or sugar residue, or taken together form a heterocycle,
m is an integer equal to 0 or 1,
n is an integer between 1 and 6 inclusive,
p is an integer between 1 and 6 inclusive,
X represents O or S(O)$_q$,
Y represents O, S(O)$_q$ or N—$R_7''$,
q is an integer between 0 and 2 inclusive,
$R_6''$ represents a hydrogen atom, a halogen atom, an alkyl group having 1 to 6 carbon atoms or an —O—$R_4''$ group,
$R_7''$ represents a hydrogen atom, an alkyl group having 1 to 6 carbon atoms or a —CO—$R_9''$ group,
$R_8''$ represents a mono- or polyhydroxyalkyl group the hydroxy groups of which are optionally protected in the form of methoxy, ethoxy, acetoxy or acetonide, a —CO—$R_8''$ group, an optionally substituted aryl or aralkyl group,
$R_9''$ represents an alkyl group having 1 to 6 carbon atoms,
$R_{10}''$ represents a hydrogen atom, an alkyl group, an alkenyl group, a mono- or polyhydroxyalkyl group the hydroxy groups of which are optionally protected in the form of methoxy, ethoxy, acetoxy or acetonide, an optionally substituted aryl or aralkyl group, or a sugar, amino acid or peptide residue, and the optical and geometrical isomers of said compounds of formula (II) as well as the pharmaceutically acceptable salts thereof.

Preferably, the compound has the formula (II) wherein:
R$_1$" represents a —CO—R$_8$" group with R$_5$" representing an —OR$_{10}$" group, R$_{10}$" being a hydrogen atom,
Ar" represents a group having the formula (c) with R$_6$" representing a hydrogen atom,
R$_2$" represents an —OCH$_3$ group, and
R$_3$" represents a hydrogen atom.

Advantageously, the compound of formula (II) is 6-[3-(1-adamantyl)-4-methoxyphenyl]-2-naphthoic acid or adapalene.

An object of the invention relates to a composition, preferably in topical form, comprising ivermectin and adapalene in a physiologically acceptable medium.

In another particular embodiment, the agonist compound for at least one of the retinoic acid receptors has the formula (III):

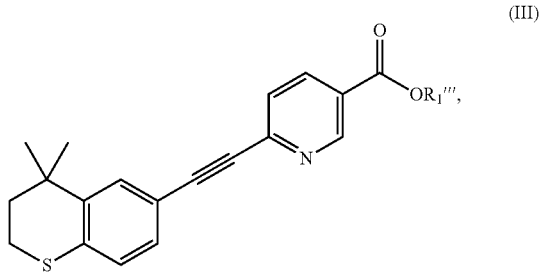

wherein:
R$_1$'" represents a hydrogen atom, an alkyl group having 1 to 18 carbon atoms, an alkenyl group having 1 to 18 carbon atoms, an alkynyl group having 1 to 18 carbon atoms, an aryl, heteroaryl, cycloalkyl or heterocycloalkyl group.

In a preferred embodiment, the compound has the formula (III), wherein R1'" represents an alkyl group having 1 to 18 carbon atoms, preferably 1 to 6 carbon atoms, and more preferably 2 carbon atoms.

Advantageously the compound of formula III is ethyl 6-[2-(4,4-dimethylthiochroman-6-yl)ethynyl]nicotinate or tazarotene.

In another particular embodiment, the agonist compound for at least one of the retinoic acid receptors has the formula (IVA) or (IVB):

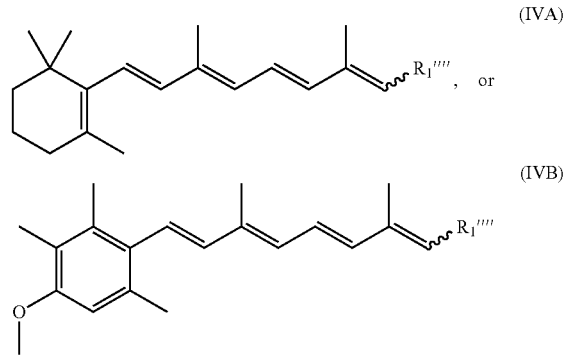

wherein:
R$_1$□ represents a —CH$_2$OH or —CHO group, or a CO$_2$R$_2$□ group wherein R$_2$□ represents a hydrogen atom, an alkyl group having 1 to 18 carbon atoms, an alkenyl group having 1 to 18 carbon atoms, an alkynyl group having 1 to 18 carbon atoms, an aryl, heteroaryl, cycloalkyl or heterocycloalkyl group.

Preferably, R$_1$□ represents a —CH$_2$OH or —CHO group, or a CO$_2$R$_2$□ group wherein R$_2$□ represents a hydrogen atom, or an alkyl group having 1 to 6 carbon atoms, preferably 2 carbon atoms.

Advantageously, the compound of formula (IVA) or (IVB) is retinoic acid, retinol, retinal, etretinate or acitretin.

In another particular embodiment, the agonist compound for at least one of the retinoic acid receptors is bexarotene having the formula (V):

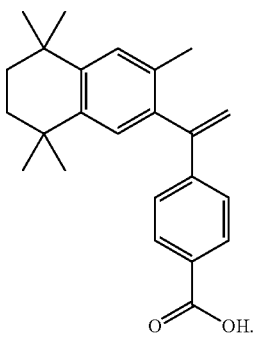

In the context of the invention, the terms below have the following meanings:

The term "alkyl" represents a saturated, linear or branched aliphatic group, typically having 1 to 18 carbon atoms, 1 to 10 carbon atoms, preferably 1 to 6 carbon atoms and more preferably 1 to 4 carbon atoms. For example, as an alkyl group having 1 to 10 carbon atoms, mention may be made of methyl, ethyl, isopropyl, butyl, tert-butyl, hexyl, nonyl and dodecyl groups. Alkyl groups having 1 to 6 carbon atoms include, for example, methyl, ethyl, isopropyl, butyl, tert-butyl and hexyl groups.

The term "alkenyl" represents an alkyl group as defined above further comprising one or more double bonds.

The term "alkynyl" represents an alkyl group as defined above further comprising one or more triple bonds.

The term "alkoxy" represents an alkyl group as defined above and linked to the molecule by an —O— (ether) bond. For example, an alkoxy group having 1 to 6 carbon atoms includes methoxy, ethoxy, propyloxy, isopropyloxy, butyloxy, isobutyloxy, tert-butyloxy, pentyloxy and hexyloxy groups.

The term "monohydroxyalkyl" represents an alkyl group as defined above substituted by a hydroxy group. For example, mention may be made of hydroxymethyl, 2-hydroxyethyl, 2- or 3-hydroxypropyl groups.

The term "polyhydroxyalkyl" represents an alkyl group as defined above substituted by at least two hydroxy groups. For example, mention may be made of 2,3-hydroxypropyl, 2,3,4-trihydroxybutyl, 2,3,4,5-tetrahydroxypentyl groups or the pentaerythritol residue.

The term "halogen" corresponds to a fluorine, chlorine, bromine or iodine atom.

The term "Ar" or "aryl" corresponds to a mono- or bicycle having 6 to 12 carbon atoms of formula $C_nH_{(n-2)}$. For example, mention may be made of phenyl, biphenyl or naphthyl groups.

The term "heteroaryl" corresponds to an aromatic mono- or polycycle comprising between 5 and 14 atoms with at least one heteroatom such as a nitrogen atom, an oxygen atom or a sulfur atom. As examples of a heteroaryl, mention may be made of the following groups: pyridyl, dihydropyridyl, thiazolyl, thiophenyl, furanyl, azocinyl, pyranyl, pyrrolyl, pyrazolyl, imidazolyl, triazolyl, tetrazolyl, benzofuranyl, thianaphthalenyl, indolyl, indolenyl, quinolinyl, isoquinolinyl, benzimidazolyl, pyrrolinyl, tetrahydroquinolinyl, tetrahydroisoquinolinyl, triazinyl, 6H-1,2,5-thiadiazinyl, 2H,6H-1,5,2-dithiazinyl, thianthrenyl, isobenzofuranyl, chromenyl, xanthenyl, phenoxanthinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, pyrimidinyl, pyrazinyl, s-triazinyl, oxazolyl and thiofuranyl.

The term "cycloalkyl" corresponds to an alkyl group as defined above linked to by a bond at its two ends. For example, mention may be made of cyclopropyl, cyclobutyl, cyclopentyl and cyclohexyl as cycloalkyls having 3 to 6 carbon atoms.

The term "heterocycloalkyl" represents a cycloalkyl group as defined above with at least one heteroatom such as a nitrogen atom, an oxygen atom or a sulfur atom.

The term "aralkyl" corresponds to an aryl group linked to an alkyl group, as they are defined above.

By "sugar residue" is meant a residue derived notably from glucose, galactose, mannose or glucuronic acid.

By "amino acid residue" is meant notably a residue derived from an amino acid such as lysine, glycine or aspartic acid and by "peptide residue" is meant more particularly a dipeptide or tripeptide residue derived from the combining of amino acids.

The " ⁀ " bond found notably in the formulae (IVA) and (IVB) represents the two types of isomerism, Z and E.

The expression "pharmaceutically acceptable salt(s)" refers to the salts of a compound of interest having the desired biological activity. The pharmaceutically acceptable salts comprise salts of acid or base groups present in the specified compounds. The pharmaceutically acceptable addition salts acid comprise, but are not limited to, the following salts: hydrochloride, hydrobromide, hydroiodide, nitrate, sulfate, bisulfate, phosphate, phosphate acid, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). Suitable base salts comprise, but are not limited to, aluminum, calcium, lithium, magnesium, potassium, sodium, zinc and diethanolamine salts. A list of pharmaceutically acceptable salts is notably published in the review by Berge et al. (J. Pharm. Sci. 1977, 66 (1), 1-19).

The RAR and RXR agonist compounds as described above make it possible to treat acne, notably by acting on the noninflammatory lesions of acne, by their anticomedogenic properties, and their effects on keratinocyte differentiation and proliferation.

In a particular embodiment, the agonist compound for at least one of the retinoic acid receptors present in the composition makes up between 0.001 and 10%, preferably between 0.001 and 5%, more preferably between 0.1 and 1%, and still more preferably 0.1 or 0.3% by weight of the total weight of the composition.

Avermectins

The class of avermectins is a group of macrocyclic lactones produced by the bacterium *Streptomyces avermitilis* (Reynolds JEF (Ed) (1993) Martindale. The extra pharmacopoeia. 29th Edition. Pharmaceutical Press, London). Among these macrocyclic lactones belonging to the class of avermectins, mention may be made of ivermectin, avermectin, abamectin, doramectin, eprinomectin, selamectin, aversectin B, AB or C, emamectin Bib and the derivatives thereof, or latidectin. According to the invention, the compound from the family of avermectins is preferably ivermectin.

Ivermectin is a mixture of 22,23-dihydroavermectin $B_{1a}$ and 22,23-dihydroavermectin $B_{1b}$. Ivermectin contains mainly 22,23-dihydroavermectin $B_{1a}$.

Ivermectin is known in the prior art for its antiparasitic properties, notably against *Demodex*, and its anthelminthic properties. In the mid-1980s, the molecule was presented as a broad-spectrum antiparasitic medicinal product for veterinary use (Campbell, W. C., et al., (1983). Ivermectin: a potent new antiparasitic agent. Science, 221, 823-828). It is effective against most common intestinal worms (except tapeworms), most Acari, and a few lice. It has a high affinity for glutamate-gated chloride channels, in particular those gated by the neurotransmitter GABA (gamma-aminobutyric acid), present in the nerve and muscle cells of invertebrates, conferring an antiparasitic activity thereon. More particularly, its binding on these channels promotes an increase in membrane permeability to chloride ions, leading to hyperpolarization of the nerve or muscle cell. The result is neuromuscular paralysis that can lead to the death of certain parasites. Ivermectin also interacts with other chloride channels. Ivermectin has also been used in the treatment of acne vulgaris. The U.S. Pat. No. 6,399,652 describes the use of ivermectin in the treatment of acne in addition to another composition containing another active agent which may be benzoyl peroxide, resorcinol, salicylic acid, an opioid, tretinoin, an antibiotic or isotretinoin.

The presence of ivermectin in the compositions of the invention advantageously makes it possible, by its anti-inflammatory properties, to treat the inflammatory lesions of acne and to improve skin tolerance by reducing the irritating effect of retinoic acid receptor agonist compounds. Moreover, ivermectin also makes it possible to reduce and eliminate the parasite *Demodex*, which in acne patients is observed to have a higher density (Zhao et al., J Zhejiang Univ Sci B., 2012, 13, 192-202).

In a particular embodiment, the compound from the family of avermectins present in the composition makes up between 0.001 and 10%, preferably between 0.001 and 5%, more preferably between 0.1 and 2%, and still more preferably 1% by weight of the total weight of the composition.

Additives

The compositions of the invention may comprise a physiologically acceptable medium, i.e., a medium compatible with the skin, the mucous membranes and/or the hair, hairs and nails. The compositions of the invention may also comprise a pharmaceutically or cosmetically acceptable carrier, i.e., a carrier suitable for use in contact with human cells, without toxicity, intolerance, irritation, undue allergic response and the like, and proportionate to a reasonable risk-benefit ratio.

The compositions of the invention may further comprise any additive or adjuvant commonly used in the pharmaceutical, dermatological or cosmetics field, compatible with the compound from the family of avermectins and the agonist compound for at least one of the retinoic acid receptors present.

Particular mention may be made of sequestrants, chelators, antioxidants, sunscreens, preservatives, for example DL-alpha-tocopherol, fillers, electrolytes, humectants, dyes, common inorganic or organic acids or bases, fragrances, essential oils, cosmetic active agents, moisturizers, vitamins, essential fatty acids, sphingolipids, self-tanning compounds such as DHA, agents that soothe and protect the skin such as allantoin, penetration agents, emulsifiers, gelling agents, thickeners, buffers, lipophilic excipients, disintegrants, solubilizers, compression agents or a mixture thereof. Of course, the person skilled in the art will take care to choose this or these optional additional compounds, and/or the amount thereof, in such a way that the advantageous properties of the composition according to the invention are not, or are not substantially, altered.

As preservatives or antibacterial agents, mention may be made by way of example of quaternary ammoniums such as benzalkonium chloride; phenoxyethanol; benzylic alcohol; benzoyl peroxide, dapsone, clindamycin, salicylic acid, diazolidinyl urea; parabens, such as methylparaben, propylparaben or butylparaben; benzoic acid and the sodium or potassium salts thereof such as sodium benzoate; sorbic acid and the sodium or potassium salts thereof such as potassium sorbate; mercury derivatives such as phenylmercury salts (acetate, borate or nitrate) or thiomersal; or mixtures thereof.

As humectants, particular mention may be made of glycerin and sorbitol.

As chelators, mention may be made by way of example of ethylenediaminetetraacetic acid (EDTA), as well as the derivatives or salts thereof, dihydroxyethylglycine, citric acid, tartaric acid or mixtures thereof.

As penetration agents, particular mention may be made of propylene glycol, dipropylene glycol, propylene glycol dipelargonate, lauroglycol and ethoxydiglycol.

As fats usable in the invention, nonrestrictive mention may be made of oils and in particular mineral oils (vaseline oil), oils of plant origin (avocado oil, soybean oil), oils of animal origin (lanolin), synthetic oils (perhydrosqualene), silicone oils (cyclomethicone) and fluorinated oils (perfluoropolyethers). Fatty alcohols such as cetyl alcohol, fatty acids, waxes and gums, particularly silicone gums, may also be used as fats.

As emulsifiers and co-emulsifiers usable in the invention, mention may be made for example of esters of fatty acid and polyethylene glycol such as PEG-100 stearate, PEG-50 stearate and PEG-40 stearate; esters of fatty acid and polyol such as glyceryl stearate, sorbitan tristearate and oxyethylene sorbitan stearates available under the trade names Tween 20 or Tween 60, for example; and mixtures thereof.

As gelling agents, by way of non-limiting examples, mention may be made of the family of polyacrylamides such as the mixture sodium acryloyldimethyltaurate copolymer/isohexadecane/polysorbate 80 sold under the name Simulgel™ 600 by the company Seppic™, the mixture polyacrylamide/C13-14 isoparaffin/laureth-7 such as, for example, that sold under the name Sepigel 305™ by the company Seppic™, the family of acrylic polymers coupled to hydrophobic chains such as PEG-150/decyl/SMDI copolymer sold under the name Aculyn 44™ (polycondensate comprising at least as elements, a polyethyleneglycol with 150 or 180 moles of ethylene oxide, decyl alcohol and methylene bis(4-cyclohexylisocyanate) (SMDI), at 35% by weight in a mixture of propyleneglycol (39%) and water (26%)), the family of modified starches such as the modified potato starch sold under the name Structure Solanace™ or mixtures thereof.

The preferred gelling agents are derived from the family of polyacrylamides such as Simulgel 600™ or Sepigel 305™ or mixtures thereof.

The composition may comprise one or more thickeners, making it possible to obtain a suitable viscosity, selected from the group consisting of polysaccharides, cellulose derivatives and Carbopol®-type carboxyvinyl polymers. These polymers comprise, but are not limited to, Carbopol® 934P, Carbopol® 71G, Carbopol® 971P and Carbopol® 974P.

The composition may comprise one or more thickeners selected from cellulose derivatives. The cellulose derivatives usable as thickeners include, but are not limited to, methylcellulose, ethylcellulose, ethylmethylcellulose, carboxymethylcellulose, sodium carboxymethylcellulose and hydroxyalkylcelluloses such as hydroxyethylcellulose, hydroxymethylcellulose, hydroxypropylcellulose and hydroxypropylmethylcellulose, and a combination thereof.

The composition may comprise one or more thickeners selected from polysaccharides. The polysaccharides usable as a thickener include, but are not limited to, xanthan gum, gum tragacanth, carrageenans such as λ-carrageenan, κ-carrageenan or ι-carrageenan, galactomannans such as carob seed flour, guar seed flour or tara seed flour, gellan gum, gum arabic, gum karaya, pectins, starch and derivatives thereof obtained by esterification or etherification, and tamarind, and a combination thereof.

The composition may also comprise, as thickeners, a mixture of one or more cellulose derivatives and one or more polysaccharides.

These additives may be present in the composition in a proportion of 0.0001 to 10% by weight in relation to the total weight of the composition. The concentration of these active ingredients and/or additives in the composition may vary according to the nature of said additives and the mode of administration envisaged.

Application

The administration may be carried out by oral, topical, ocular, intraocular, intravenous, parenteral, subcutaneous, epicutaneous, intradermal, transdermal, intramuscular, enteral, rectal, intranasal, sublingual, buccal or intra-respiratory route or by nasal inhalation.

When the administration is carried out topically on the skin, the composition may be described as a dermatological composition. The composition intended to be administered topically is more particularly intended for treating the skin and the mucous membranes. By "topical application" is meant the fact of applying or spreading the composition according to the invention on the surface of the skin or a mucous membrane.

Among these routes of administration, the topical route is particularly preferred.

For topical application, compositions are envisaged in the form of solutions, lotions, gels, salves, milk-type emulsions having a fluid or semi-fluid consistency obtained by dispersion of a fatty phase in an aqueous phase (O/W) or the reverse (W/O), or powders, saturated buffers, sprays, suspensions or emulsions having a soft, semi-fluid or solid consistency of the cream or ointment type, or microemulsions, microcapsules, microparticles or vesicular dispersions of the ionic and/or nonionic type. They may also appear in the form of microspheres or nanospheres or lipid or polymer vesicles or polymer patches and hydrogels allowing controlled release. These compositions are prepared according to the usual methods.

For topical administration, the composition advantageously appears as a gel, a lotion or a cream.

A preferred composition of the invention is a topical composition comprising between 0.001 and 10% by weight of the compound from the family of avermectins and between 0.001 and 5% by weight of the agonist compound for at least one of the retinoic acid receptors in relation to the total weight of the composition.

Preferably, the compound from the family of avermectins makes up between 0.001 and 5%, between 0.1 and 2%, and more preferably 1% by weight of the total weight of the composition. Preferably, the agonist compound for retinoic acid receptors makes up between 0.001 and 10%, preferably between 0.001 and 5%, more preferably between 0.1 and 1%, and still more preferably 0.1 or 0.3% by weight of the total weight of the composition.

According to a preferred embodiment, the composition according to the invention comprises 1% by weight in relation to the total weight of the composition of a compound from the family of avermectins, preferably ivermectin, and 0.1% or 0.3% by weight in relation to the total weight of the composition of an agonist compound for at least one of the retinoic acid receptors, preferably adapalene.

According to another preferred embodiment, the composition according to the invention comprises 1% by weight in relation to the total weight of the composition of a compound from the family of avermectins, preferably ivermectin, and between 0.001 and 1%, preferably 0.005% by weight in relation to the total weight of the composition of an agonist compound for at least one of the retinoic acid receptors, preferably the compound 3"-tert-butyl-4'-(2-hydroxyethoxy)-4"-pyrrolidin-1-yl-[1,1';3',1" ]-terphenyl-4-carboxylic acid.

The present invention also relates to a kit comprising (a) a first composition comprising a compound from the family of avermectins, preferably ivermectin, and (b) a second composition, distinct from the first, comprising an agonist compound for at least one of the retinoic acid receptors, preferably adapalene.

In a particular embodiment, the kit as defined above is used in the treatment of acne, preferably in a concomitant or separate manner.

In another particular embodiment, the kit is intended for topical application.

Preferably, the composition (a) of the kit comprises between 0.001 and 10%, preferably between 0.1 and 2%, and more preferably 1% by weight of ivermectin in relation to the total weight of the composition. For example, mention may be made of the formulation marketed by Galderma under the name Soolantra® comprising 1% by weight of ivermectin.

Preferably, the composition (b) of the kit comprises between 0.001 and 10%, preferably between 0.001% and 5%, more preferably between 0.1 and 1%, and still more preferably 0.1% or 0.3% by weight of adapalene in relation to the total weight of the composition. For example, mention may be made of the range of formulations marketed by Galderma under the name Differin® and notably Differin® 0.3% and Differin® 0.1% comprising 0.3% and 0.1% by weight of adapalene, respectively.

In the context of the invention, the terms "treatment" or "to treat" refer to improvement, prophylaxis or reversal of a disease or disorder, or at least of one symptom that can be distinguished therefrom. These terms also include improvement, prophylaxis or reversal of at least one measurable physical parameter associated with the disease or disorder being treated, that is not necessarily discernible in or by the treated subject. The terms "treatment" or "to treat" also refer to inhibition or slowing of the progression of a disease or disorder, physically, for example, stabilization of a discernible symptom, physiologically, for example, stabilization of a physical parameter, or both. These terms further refer to the delaying of the onset of a disease or disorder.

In certain embodiments, the compounds of interest are administered as a preventive measure. In the present context, this preventive measure refers to a reduction in the risk of acquiring a specified disease or disorder but also a reduction, an inhibition or a slowing of the onset of the symptoms related to this disease, namely acne. The characteristic symptoms of acne are, for example, open and/or closed comedones, papules, pustules, nodules and cysts appearing mainly on the face, neck and thorax, i.e., the regions of the skin where the greatest number of sebaceous glands are found.

In the context of the invention, by "treatment of acne" is meant the treatment of acne in all its various forms. The treatment of acne includes acne conglobata, acne keloidalis nuchae, drug-induced acne, recurrent acne miliaris, acne necrotica, acne neonatorum, premenstrual acne, occupational acne, senile acne, solar acne, acne inversa and acne vulgaris.

Within the meaning of the present invention, by "patient" is meant any mammal, and more particularly human beings, men or women, children and adolescents The amount of the compound from the family of avermectins and the agonist compound for at least one of the retinoic acid receptors and, optionally, other additives to be implemented according to the invention actually administered depends on the therapeutic or cosmetic effect desired, and may thus vary greatly. The person skilled in the art, particularly the doctor, can easily, based on his general knowledge, determine the suitable amounts. Thus, and according to a preferred embodiment, the pharmaceutical composition(s) is/are administered 1 to 2 times/day. Preferably, the treatment may have a duration of 1 week to 6 months, which may be repeated, and preferably of 2 weeks to 4 months.

The treatments may be repeated in cycles with or without a rest period.

In the context of the invention, by "therapeutically effective amount" is meant the therapeutic amount that prevents, stops or reduces the deleterious effects of the acne treated in the patient. It is understood that the amount administered may be adapted by the person skilled in the art according to the patient, the type of acne, the mode of administration, etc.

The following examples illustrate the invention without limiting its scope.

EXAMPLES

Example 1: Impact on the Expression of Inflammatory Cytokines

Materials and Methods

Overexpression of inflammatory cytokines was shown in patients with acne. Indeed, the study by the team of Sugisaki et al. (J Dermatol Sci. 2009; 55(1):47-52) showed an increase in the expression of interferon gamma, interleukin 12p40 and IL8 by peripheral blood mononuclear cells from patients with acne. Likewise, the team of Kistowska et al. revealed the production of several inflammatory cytokines (IL-1β, IL-6, TNFα and IL-8) by monocytes exposed to the bacterium *Propionibacterium acnes*, whose role in acne pathology is recognized (Kistowska et al., J Invest Dermatol. 2014; 134(3):677-85).

Consequently, the expression of certain of these cytokines with ivermectin alone, with the retinoic acid receptor agonist alone, and with the combination of ivermectin with a retinoic acid receptor agonist, was measured.

More precisely, peripheral blood mononuclear cells were incubated for 24 hours in 96-well plates coated with an anti-CD3 antibody in order to activate said cells and to induce secretion of inflammatory cytokines, in the presence or the absence of the various active agents and the combination to be tested.

After collecting the supernatants, the production of tumor necrosis factor (TNFα), interleukin 12p40 (IL12p40) and interferon gamma (IFNγ) was quantified using an immunoassay.

Results

The results are presented in the Figures. These in vitro results show that the production of TNFα, IL12p40 and IFNγ is significantly decreased by the combination of ivermectin and a retinoic acid receptor agonist, unlike what is observed with ivermectin or the retinoic acid receptor agonist alone.

These results thus make it possible to demonstrate an improved effect of the combination of ivermectin and a retinoic acid receptor agonist for decreasing the production of certain inflammatory cytokines observed in patients with acne. More precisely, these in vitro results made it possible to demonstrate a synergistic effect of the combination of ivermectin and a RAR agonist compound for treating and/or preventing acne.

Example 2: Comparative Clinical Study

A comparative study was carried out among patients with acne. The patients initially received a first treatment (Treatment A) with topical or oral retinoids, in combination with other active ingredients commonly used to improve the efficacy or the tolerance of retinoids. These same patients then received a second treatment (Treatment B) containing ivermectin and were followed over several months.

The satisfaction score illustrated in Table 1 below is obtained for each treatment and is ascertained on a scale from 0 to 5.

TABLE 1

| Satisfaction score | |
|---|---|
| SCORE | SIGNIFICANCE |
| 0 | Absolutely not satisfied |
| 1 | Slightly satisfied |
| 2 | Fairly satisfied |
| 3 | Satisfied |
| 4 | Very satisfied |
| 5 | Extremely satisfied |

The active ingredients used and the mode of administration of each treatment (mode of administration and duration of treatment), as well as the patient's satisfaction score obtained for each treatment, are illustrated in Table 2 below.

Treatment A corresponds notably to the use of products comprising one or more retinoids currently on the market, sold with or without a prescription, and commonly recommended by dermatologists for treating acne. By way of example, mention may be made of: Differin 0.3%®, Epiduo®, Metrogel® and Epiduo Forte® marketed by Galderma Laboratories, Accutane® from Roche Laboratories, and Ziana® from Medicis Pharmaceutical Corp.

The retinoids present in these products and used by the followed patients are notably adapalene, retinol, tazarotene, tretinoin and isotretinoin.

The antibacterial agents used in combination with these retinoids are notably benzoyl peroxide, dapsone, clindamycin phosphate and salicylic acid.

TABLE 2

| Patient | Treatment (ingredients) | Mode of administration | Score | Observations |
|---|---|---|---|---|
| 1 | A: retinol 0.05%, benzoyl peroxide 10% | Application to the entire face every day at bedtime for 6 months. | 0 | Dropped out |
| | B: ivermectin 1%, adapalene 0.1%, benzoyl peroxide 0.1% | Application to the entire face every day at bedtime for 2 months. | 5 | Maintained over time |
| 2 | A: retinol 0.05%, benzoyl peroxide 2.5%, salicylic acid 0.5% | Application to the entire face every day at bedtime. | 0 | Not tolerated |
| | B: ivermectin 1%, adapalene 0.1%, benzoyl peroxide 2.5% | Application to the entire face every day at bedtime for 2 months. | 4 | Maintained over time |
| 3 | A. clindamycin phosphate 1.2%, tretinoin 0.025%, adapalene 0.1%, benzoyl peroxide 2.5%, dapsone 5% | Application to the entire face every day at bedtime, except for dapsone which is applied to the entire face every day in the morning, for 14 months. | 1 | Very little efficacy |
| | B: ivermectin 1%, adapalene 0.3%, benzoyl peroxide 2.5% | Application to the entire face every day at bedtime for 6 weeks. | 4 | Maintained over time |

TABLE 2-continued

| Patient | Treatment (ingredients) | Mode of administration | Score | Observations |
|---|---|---|---|---|
| 4 | A: adapalene 0.3% | Application to the entire face every day at bedtime for 10 months. | 1 | Significant irritation |
|  | B: ivermectin 1%, adapalene 0.3% | Application to the entire face every day at bedtime for 2 weeks. | 4 | Maintained over time |
| 5 | A: tretinoin 0.05% | Application to the entire face every day at bedtime for 6 months. | 0 | Dropped out |
|  | B: ivermectin 1%, tretinoin 0.05% | Application to the entire face every day at bedtime for 1 month. | 5 | Maintained over time |
| 6 | A: adapalene 0.3%, benzoyl peroxide 2.5% | Application to the entire face every day at bedtime for 6 months. | 0 | Dropped out |
|  | B: ivermectin 1%, adapalene 0.3%, benzoyl peroxide 2.5% | Application to the entire face every day at bedtime for 2 months. | 5 | Maintained over time |
| 7 | A: tretinoin 0.05% | Application to the entire face every day at bedtime for several years. | 0 | Dropped out |
|  | B: ivermectin 1%, adapalene 0.3%, benzoyl peroxide 2.5% | Application to the entire face every day at bedtime for a few weeks. | 5 | Maintained over time |
| 8 | A: adapalene 0.3%, tretinoin 0.05%, tazarotene 0.1%, oral isotretinoin 1-200 mg/kg | Application to the entire face every day at bedtime for several years, except for isotretinoin which is administered orally. | 1 | Dropped out |
|  | B: ivermectin 1%, adapalene 0.3% | Application to the entire face every day at bedtime for a few weeks. | 5 | Maintained over time |
| 9 | A: adapalene 0.3%, benzoyl peroxide 2.5% | Application to the entire face every day at bedtime. | 0 | Not tolerated |
|  | B: ivermectin 1%, adapalene 0.3%, benzoyl peroxide 2.5% | Application to the entire face every day at bedtime for a few weeks. | 5 | Maintained over time |
| 10 | A: adapalene 0.3% | Application to the entire face every day at bedtime. | 0 | Not tolerated |
|  | B: ivermectin 1%, adapalene 0.3% | Application to the entire face every day at bedtime for a few weeks. | 5 | Maintained over time |
| 11 | A: dapsone 5%, adapalene 0.3%, retinol 0.05% | Application to the entire face every day at bedtime for one week, except for dapsone which is applied every day in the morning for one week. | 0 | Not tolerated |
|  | B: ivermectin 1%, retinol 0.05% | Application to the entire face every day at bedtime for 2 weeks. | 5 | Maintained over time |
| 12 | A: retinol 0.05%, clindamycin phosphate 1.2%, tretinoin 0.025%, metronidazole 1% | Application to the entire face every day at bedtime. | 0 | Not tolerated |
|  | B: ivermectin 1%, retinol 0.05% | Application to theentire face every day at bedtime for 3 months. | 4 | Maintained over time |
| 13 | A: adapalene 0.1%, benzoyl peroxide 2.5%, dapsone 5% | Application to the entire face every day at bedtime, except for dapsone which is applied every day in the morning. | 0 | Not tolerated |
|  | B: ivermectin 1%, adapalene 0.1%, benzoyl peroxide 2.5% | Application to the entire face every day at bedtime for 1 month. | 5 | Maintained over time |
| 14 | A: retinol 0.05%, adapalene 0.3% | Application to the entire face every day at bedtime. | 0 | Not tolerated |
|  | B: ivermectin 1%, adapalene 0.1%, benzoyl peroxide 2.5% | Application to the entire face every day at bedtime for 1 month. | 5 | Maintained over time |
| 15 | A: tretinoin 0.05%, retinol 0.05% | Application to the entire face every day at bedtime. | 0 | Not tolerated |
|  | B: ivermectin 1%, retinol 0.05% | Application to the entire face every day at bedtime for 2 months. | 5 | Maintained over time |
| 16 | A: retinol 0.05% | Application to the entire face every day at bedtime for several years. | 0 | Dropped out |

TABLE 2-continued

| Patient | Treatment (ingredients) | Mode of administration | Score | Observations |
|---|---|---|---|---|
| | B: ivermectin 1%, adapalene 0.1%, benzoyl peroxide 2.5% | Application to the entire face every day at bedtime for 1 month. | 5 | Maintained over time |

The results presented above show the beneficial effects of ivermectin in retinoid-based acne treatments.

These beneficial effects were observed in terms of tolerance to retinoids, with notably a significant decrease in skin irritation, which is often associated with retinoid use.

These beneficial effects were also observed in terms of the efficacy of the treatment against acne, with a greater decrease in pimples and red patches obtained with a retinoid-based treatment comprising ivermectin compared with a retinoid-based treatment not comprising ivermectin.

The invention claimed is:

1. A topical composition, consisting of:
    (a) 0.1% to 2% by weight, relative to the total weight of the composition, of ivermectin;
    (b) 0.001% to 1% by weight, relative to the total weight of the composition, of trifarotene; and
    (c) one or more pharmaceutically acceptable excipients.

2. The composition according to claim 1, wherein the ivermectin is present in an amount of 1% by weight, relative to the total weight of the composition, and the trifarotene is present in an amount from 0.005% to 1% by weight, relative to the total weight of the composition.

3. The composition according to claim 1, wherein the composition is formulated for topical administration.

4. The composition according to claim 1, wherein the composition is in the form of a gel, a lotion or a cream.

5. The composition according to claim 1, wherein the ivermectin is present in an amount of 1% by weight, relative to the total weight of the composition.

6. The composition according to claim 1, wherein the trifarotene is present in an amount of 0.005% by weight, relative to the total weight of the composition.

* * * * *